(12) United States Patent
Margueritte

(10) Patent No.: US 8,869,978 B2
(45) Date of Patent: Oct. 28, 2014

(54) DEVICE FOR STORING SUTURING THREADS

(76) Inventor: Philippe Margueritte, Le Rheu (FR)

(*) Notice: Subject to any disclaimer, the term of this patent is extended or adjusted under 35 U.S.C. 154(b) by 530 days.

(21) Appl. No.: 12/596,183

(22) PCT Filed: Apr. 8, 2008

(86) PCT No.: PCT/FR2008/000491
§ 371 (c)(1),
(2), (4) Date: Mar. 5, 2010

(87) PCT Pub. No.: WO2008/142272
PCT Pub. Date: Nov. 27, 2008

(65) Prior Publication Data
US 2010/0187134 A1    Jul. 29, 2010

(30) Foreign Application Priority Data

Apr. 17, 2007  (FR) .................................... 07 02769

(51) Int. Cl.
*A61B 17/06*   (2006.01)

(52) U.S. Cl.
CPC . *A61B 17/06114* (2013.01); *A61B 2017/06147* (2013.01); *A61B 2017/06142* (2013.01); *A61B 17/06138* (2013.01); *A61B 17/06161* (2013.01); *A61B 17/06133* (2013.01)
USPC ........................... 206/63.3; 206/370; 206/495

(58) Field of Classification Search
USPC .................. 206/370, 63.3, 495, 380, 382, 383
See application file for complete search history.

(56) References Cited

U.S. PATENT DOCUMENTS

| | | | |
|---|---|---|---|
| 3,759,376 A | | 9/1973 | Lisowski |
| 3,940,873 A | * | 3/1976 | Lawless ......................... 43/57.1 |
| 4,008,002 A | | 2/1977 | Niemiec et al. |
| 4,008,802 A | * | 2/1977 | Freitag ........................ 206/63.3 |
| 4,121,711 A | | 10/1978 | Bolanowski |
| 4,151,913 A | * | 5/1979 | Freitag ........................... 206/370 |
| 4,182,448 A | | 1/1980 | Huck et al. |
| 4,243,140 A | | 1/1981 | Thrun |
| 4,591,048 A | * | 5/1986 | Eldridge, Jr. ................. 206/63.3 |
| 4,637,513 A | * | 1/1987 | Eldrige, Jr. ................... 206/370 |
| 4,730,725 A | | 3/1988 | Marshall, Sr. et al. |

(Continued)

FOREIGN PATENT DOCUMENTS

| | | |
|---|---|---|
| EP | 0623310 A2 | 11/1994 |
| EP | 1346693 A1 | 9/2003 |
| FR | 2391735 A1 | 12/1978 |
| JP | 61142010 U | 9/1986 |

OTHER PUBLICATIONS

International Search Report, PCT/FR2008/000491, dated Nov. 18, 2008.

*Primary Examiner* — Anthony Stashick
*Assistant Examiner* — Ernesto Grano
(74) *Attorney, Agent, or Firm* — Lerner, David, Littenberg, Krumholz & Mentlik, LLP

(57) ABSTRACT

The invention relates to a device for storing and classifying at least one surgical suturing thread (3) fitted on a needle (30). This device is noteworthy in that it comprises a support (1), of which at least one part of one of the faces (11), called 'top' face, supports removable means (2) of fixing said thread (3), and in that said support (1) comprises means (5, 5') of displaying technical characteristics specific to each suturing thread (30) and/or to each needle (30) to be stored. Applicable to the medical domain.

16 Claims, 2 Drawing Sheets

(56) References Cited

U.S. PATENT DOCUMENTS

| | | | |
|---|---|---|---|
| 4,736,844 A * | 4/1988 | Scott et al. | 206/370 |
| 5,101,968 A * | 4/1992 | Henderson et al. | 206/63.3 |
| 5,249,672 A * | 10/1993 | Brown et al. | 206/63.3 |
| 5,281,391 A * | 1/1994 | Hanson et al. | 422/25 |
| 5,601,185 A | 2/1997 | Behring et al. | |
| 6,029,806 A * | 2/2000 | Cerwin et al. | 206/63.3 |
| 2005/0269228 A1 | 12/2005 | Kanner et al. | |

* cited by examiner

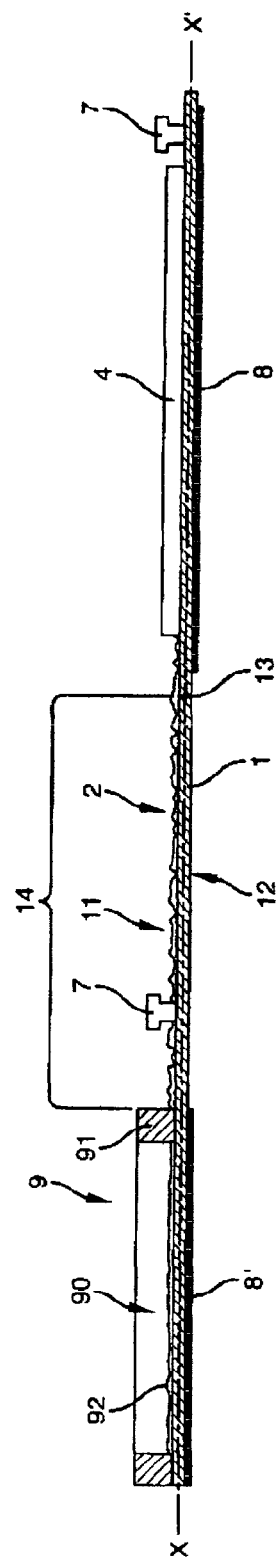

DEVICE FOR STORING SUTURING THREADS

CROSS REFERENCE TO RELATED APPLICATIONS

The present application is a national phase entry under 35 U.S.C. §371 of International Application No. PCT/FR2008/000491, filed 8 Apr. 2008, published in French, which claims the benefit of French Patent Application No. 0702769, filed 17 Apr. 2007. The disclosures of said applications are incorporated by reference herein.

CROSS-REFERENCE TO RELATED APPLICATIONS

The present application is a national phase entry under 35 U.S.C. §371 of International Application No. PCT/FR2008/000491, filed 8 Apr. 2008, published in French, which claims the benefit of French Patent Application No. 0702769, filed 17 Apr. 2007. The disclosures of said applications are incorporated by reference herein.

BACKGROUND OF THE INVENTION

The invention relates to the area of surgical instrumentation.

More precisely, it concerns a device to store and arrange or classify at least one surgical suturing thread before, during, or after its use during an operation.

When a surgeon operates on a patient, to draw the edges of the wounds or organs together, a thread called "suturing thread" is used.

These suturing threads are marketed in the form of a certain length of thread swaged to a needle. In some cases, a thread may be provided with two needles, one at each of its ends.

The suturing thread and needle(s) are marketed in a sterile pack which itself is contained inside a blister pack or aluminium sachet. The sterile pack carries indications on the technical characteristics of the thread and needle contained therein.

The needles may be straight or curved, with a round or triangular cross-section for example.

Also suturing threads are of different diameters, lengths and types in relation to the intended surgical application. In addition, some are absorbable, others are not.

In practice, surgeons operate assisted by a surgical assistant who is asked to pass the instruments needed and the suturing thread suitable for the suture to be made.

At the surgeon's request, the surgical assistant takes the sterile pack containing the appropriate suturing thread, opens it and passes the thread swaged to the needle to the surgeon by means of a needle holder.

Suturing threads can be very costly. After completing a suture, the surgeon gives back the remaining suturing thread (off-cut) and needle to the surgical assistant for their temporary storage before a second use and even a third use if the residual length of the thread so permits.

In the current state of the art, the surgical assistant simply lays the needle and remaining thread on the operating table, on the sterile surgical drapes.

It will easily be appreciated that during a long, complex surgical operation, a surgical assistant may have to classify and organize numerous residual suturing threads whose technical characteristics and those of the needle are highly different. Since the suturing threads have been taken out of their sterile pack, there is a high risk of error with respect to diameter or type of suturing thread. Also the surgical assistant runs the risk of entangling the different threads.

Additionally, the needles placed on the sterile drapes may perforate these drapes or be dropped.

If perforation goes unnoticed, there is a risk of continuing to use a needle which is no longer sterile and/or of continuing a surgical operation when the surgical drapes are no longer sterile.

If the surgical assistant realizes that the needle has perforated the sterile drapes, the needle must be discarded despite the financial loss since it is no longer sterile.

Additionally, there is a possibility that surgical assistant may suffer skin puncture with the numerous needles placed before him, which may cause accidental contamination from blood on the needle, which may be infected.

Finally, the dropping of a needle may go unnoticed, and staff who clean the operating block after the operation are also potentially exposed to blood contamination should they accidentally injure themselves with this needle.

The purpose of the invention is therefore to solve the above-mentioned disadvantages of the state of the art, and in particular to provide a device with which it is possible to store, arrange or classify the threads used for a surgical suturing:
- temporarily,
- without any risk of entangling the suturing threads or tying knots,
- avoiding loss thereof through accidental dropping,
- and by associating indications with each suturing thread and its needle, giving information on their particular technical characteristics.

A further purpose of the invention is to provide a device with which it is possible to limit the risk of surgical assistants suffering accidental skin puncture, and thereby to avoid accidents due to exposure to blood.

Finally an additional objective of the invention is to provide a device with which it is possible to store used needles before they are discarded, at lower cost than with sharps containers known in the state of the art.

SUMMARY OF THE INVENTION

For this purpose, the invention concerns a device to store and classify at least one surgical suturing thread mounted on a needle.

According to the invention, this device comprises a support of which at least part of one of the faces called the "upper" face carries means for removably attaching said thread, and said support comprises display means to display the technical characteristics particular to each suturing thread and/or each needle to be stored.

According to other advantageous, non-limiting characteristics of the invention, taken alone or in combination:
- said means for removably attaching the thread comprise a self-fastening strip;
- the device comprises means to receive the tip of the surgical needle, these means extending over said upper face of the support, in the vicinity of said means for removably attaching the thread;
- said support comprises means to attach at least part of the sterile pack inside which said suturing thread is packed and on which indications are given of the technical characteristics particular to each suturing thread and/or each needle to be stored;
- the support comprises a region carrying indications specifying the technical characteristics particular to each suturing thread and/or each needle to be stored;

the device comprises a plurality of lugs projecting from the upper face of said support, in the vicinity of said means for removably attaching the thread, and around which said suturing thread can be looped;

said support, on part of its upper face, has means to store used needles;

said support comprises a scored region able to be torn to divide said support into two parts, this scored region delimiting one portion of said support able to be folded over and fixed to said storage means to make them inaccessible;

said support comprises removable attachment means on an outer element, these means extending over its rear face opposite said front face;

said support is in the shape of a strip of flexible material;

said means for removably attaching the thread carry a series of surgical suturing threads and new needles, this series being suitable for the performing of a particular surgical operation, said support comprises a region carrying indications giving the technical characteristics particular to each of said suturing threads and/or needles of said series, and said needles are arranged facing said indications.

BRIEF DESCRIPTION OF THE DRAWINGS

Other characteristics and advantages of the invention will become apparent from the description given below with reference to the appended drawings given for indication purposes and non-limiting, which illustrate one possible embodiment thereof.

In these drawings:

FIG. 2 is a longitudinal, cross-sectional view of the device according to the invention along line II-II in FIG. 1.

DETAILED DESCRIPTION

Figure 1:
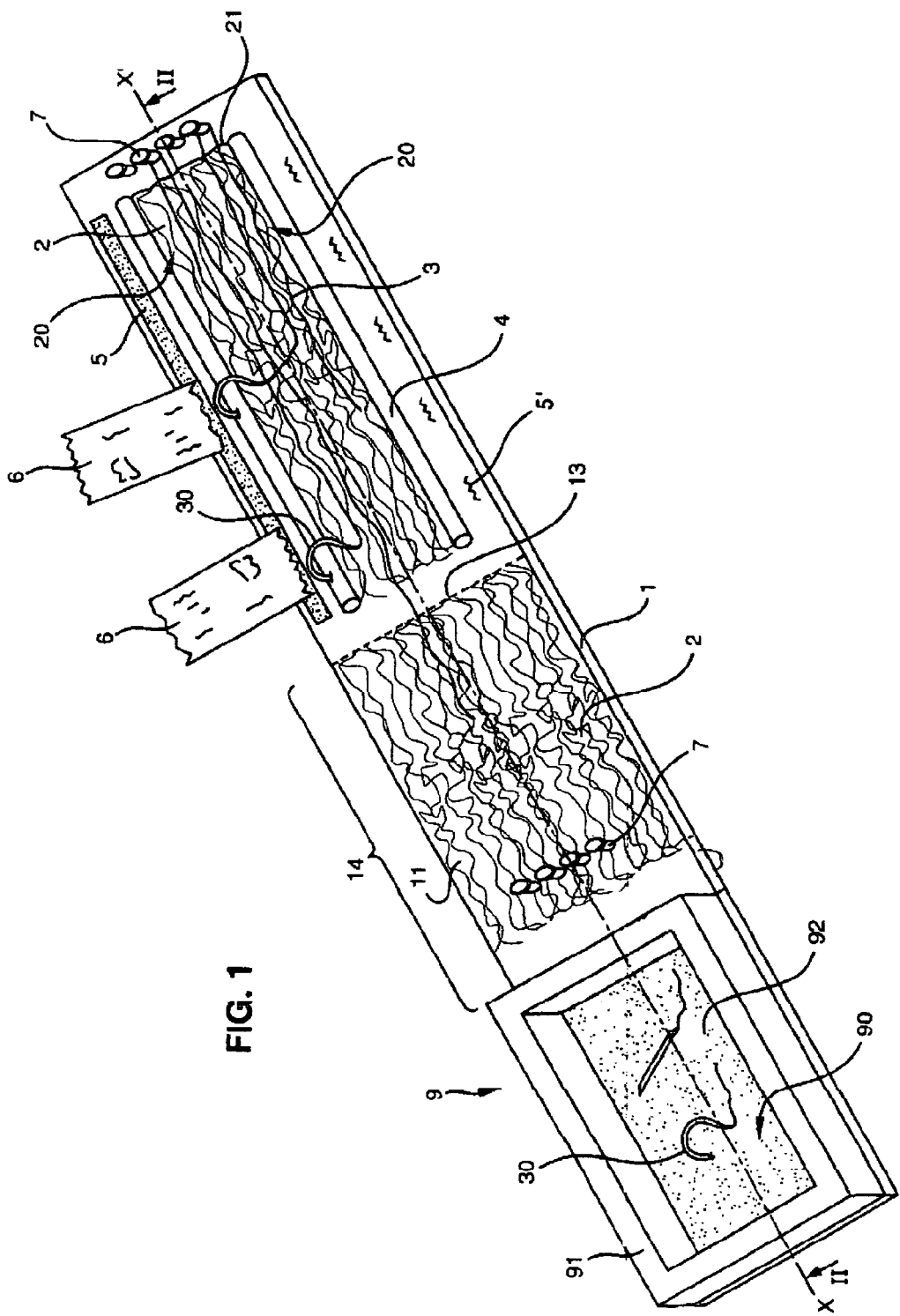
FIG. 1 is a perspective view of the device conforming to the invention.

The invention will now be described in more detail with reference to FIGS. 1 and 2.

The device conforming to the invention comprises a support 1, preferably planar or substantially planar and of narrow thickness. It comprises two opposite faces, namely an upper face 11 and a lower face 12, the references to "upper" and "lower" being made with respect to the normal position of use of the device.

Advantageously, the support 1 is made in a flexible material such as a piece of plastic or cardboard material, or a fabric able to be sterilized.

Preferably, the support 1 is in the form of an elongate strip as shown FIG. 1. However, it could also assume another shape.

At least part of the upper face 11 of the support 1 is covered with means 2 enabling the removable attachment of the suturing threads 3.

These means 2 are advantageously a self-fastening strip consisting of a barbed or hooked material e.g. the material known under the registered trademark "VELCRO".

When the suturing thread is placed over these barbs or hooks, these catch and retain the thread. This attachment is removable however, since mere pulling on the thread 3 is sufficient to remove it from said means 2.

Other types of means 2 could also be considered, such as a sheet of plastic material having channels to retain the thread.

For reasons of simplification, in the remainder of the description, only a support 1 in the form of a rectangular strip holding a self-fastening strip 2 will be described in detail.

The self-fastening strip 2 extends longitudinally over at least part of the support 1, and in FIG. 1 over at least the right half thereof.

Preferably, the device also comprises means 4 to receive the tip of the needle 30 that is joined to the thread 3.

These means 4 consist, for example, of a roll or tongue of material inside which it is possible to insert the tip of the needle, for example a plastic foam material.

These elements 4 extend longitudinally over the upper face 11 of the support 1, along at least one of the longitudinal edges 20 of the self-fastening strip 2. Preferably, these elements 4 are provided on both sides of part of the self-fastening strip 2 as illustrated FIG. 1.

These elements 4 are used to protect the surgical assistant from the risks of skin puncture mentioned above.

The device of the invention also comprises means to display the technical characteristics particular to each suturing thread and/or each needle to be stored.

These means may be of two types, respectively referenced 5 and 5'.

It has arbitrarily been chosen to show means 5 on the upper part in FIG. 1 and means 5' on the lower part. However, the support 1 could also comprise only one of these categories of means.

According to a first embodiment, the means 5 are used temporarily to attach at least part of the sterile pack 6 from which the suturing thread is taken, more precisely that part of the sterile pack which carries the characteristics of the suturing thread or suture needle under consideration.

These means 5 may for example be an adhesive surface which extends longitudinally parallel to the self-fastening strip 2 and opposite the elements 4.

According to one variant not shown in the figures, these means 5 could also consist of a slot arranged in the thickness of the support 1, and inside which the surgical assistant can insert the end part of the sterile pack 6.

The display means 5' to display the technical characteristics are pre-printed indications on the support 1, along the element 4 and/or the strip 2.

These indications 5' may, for example, relate to the diameter of the thread and/or needle used.

Advantageously, the support 1 also comprises lugs 7 projecting from the upper face 11 of the support 1, perpendicular thereto. Preferably, they are T-shaped as can be more clearly seen in the cross-sectional view FIG. 2.

The device therefore comprises at least one series of lugs 7, preferably two series, arranged in the vicinity of one or both ends 21 of the self-fastening strip 2.

When the device is in use, the surgical assistant handles the needle 30 and thread 3 by means of a needle-holder, i.e., needle clamp.

The assistant passes the suturing thread 3 through the hooks of the self-fastening strip 2 for example from left to right in FIG. 1, makes a half-turn with the thread around a lug 7, slides the thread towards the left of FIG. 1 and lodges the tip of the needle in the foam element 4.

The lug 7 is used to loop back the suturing thread. The T-shape facilitates holding of the thread 3.

The suturing thread 3 is retained by the barbs or hooks of the self-fastening strip 2, and cannot be accidentally moved even if the operator passes a sleeve for example over the device.

Advantageously, the self-fastening strip 2 is of sufficient length for the surgical assistant to be able to store a suturing thread remnant (off cut) by looping it simply two or three times around the lugs 7. Therefore the suturing thread 3 cannot become entangled and the surgical assistant can easily and visually estimate the length of remaining suturing thread which may be used for further suture of tissues.

If the device comprises pre-printed indications 5' the surgical assistant inserts the tip of the needle 30, whose thread and/or needle corresponds to these indications, opposite these indications.

Finally, advantageously, and as can be better seen FIG. 2, the support 1 on its lower face 12 opposite the self-fastening strip 2 comprises means 8 used to secure the device to the instrument table during its use. These means 8 are for example a repositionable adhesive strip or a self-fastening strip of "VELCRO" type (registered trademark).

According to one variant of embodiment shown in the left-hand part of FIG. 1, the support 1 extends beyond the self-fastening strip 2 and at its other end carries means 9 to store used needles 30.

These means 9 are for example a container 90 delimited by a rim 91 of low height. The bottom of this container 90 is covered with a layer of material 92 to which the used needles can attach.

This material 92 is for example an adhesive strip, a magnetized strip or a gel layer.

It will be noted that the rims 91 are optional. However, if they are present, they are advantageously covered with self-fastening strips of "Velcro" type (registered trademark) comprising loops and therefore able to cooperate with that part of the self-fastening strip 2 which extends between the container 90 and the tongues or rolls 4 in accordance with the functioning explained below.

Preferably, the support 1, on its lower face 12 under the container 90, also has temporary securing means 8' similar to those described previously under reference 8.

If the support 1 comprises storage means 9 for used needles, it then has a scored region 13 which extends perpendicular to its longitudinal axis X-X'.

Therefore at the end of a surgical operation, the surgical assistant removes the remnants of suturing thread 30 remaining on the self-fastening strip 2, cuts each thread 3 close to the needle 30, and places the needles inside the container 90. The assistant then tears the support 1 along the scored region 13 and folds the portion 14 of the support 1 which extends between the scored region 13 and the container 90 over the opening of this container. The self-fastening strips located on portion 14 of the support 1 and on the rim 91 cooperate with each other.

The position of the scored region 13 is such that it delimits a portion 14 of sufficient length to close the container 90 and make the needles inaccessible.

Portion 14 of the support 1 plays a twofold role of supporting the self-fastening strip 2 and acting as flap to close the container 90. The device conforming to the invention therefore additionally serves as sharps container for used needles, but at a lower cost than prior art devices.

The surgical assistant can then discard that part of the support into bins specifically dedicated to the storage of potentially contaminated needles.

According to one variant of embodiment of the invention, the device can be marketed with a series of new suturing threads 3 and new needles 30 (i.e., non-used) arranged on the self-fastening strip 2, this series of threads and needles being suitable for the performing of a particular surgical operation. In this case, the support 1 carries indications 5' specifying the technical characteristics of each of the suturing threads and/or needles of said series, and the needles 30 are inserted in the foam element 4 facing said indications 5'.

It is therefore possible to make provision for devices more specifically dedicated to a vascular or obstetrical operation for example.

The subsequent use of this device remains identical to the use described for the other embodiments. Said device dedicated to a category of surgical operation is evidently sterilized and sold in a sterile pack.

The invention claimed is:

1. A device for storing, arranging, or classifying surgical suturing threads or surgical suturing threads mounted to needles, the device comprising:
 a support having an upper face carrying a self-fastening strip adapted to removably attach with and temporarily secure at least one surgical suturing thread or at least one remnant of a suturing thread, such that said suturing thread or remnant is selectively removable from said self-fastening strip and usable in a surgical procedure, said support comprising attachment means adapted to at least temporarily connect with part of a sterile pack, wherein said support includes an indicator with information conveying to a user at least one technical characteristic particular to said suturing thread or said needle to be stored, wherein said indicator comprises a portion of a sterile pack attached to said attachment means, said sterile pack storing said suturing thread or said needle prior to attachment with said support.

2. The device according to claim 1, further comprising means to receive a tip of said needle, said means extending over said upper face of said support, in the vicinity of said self-fastening strip.

3. The device according to claim 1, wherein said support comprises a region carrying multiple indicators, each with information conveying to the user at least one technical characteristic particular to said suturing thread or said needle to be stored.

4. The device according to claim 1, further comprising a plurality of lugs projecting from said upper face of said support in the vicinity of said self-fastening strip, and around which said suturing thread or said remnant can be looped.

5. The device according to claim 1, wherein said support, on a part of said upper face thereof, has storage means to store used needles.

6. The device according to claim 5, wherein said support comprises a scored region able to be torn to divide said support into two parts, said scored region delimiting a portion of said support, which can be folded over and fixed onto said storage means to make said storage means inaccessible.

7. The device according to claim 1, wherein said support comprises removable securing means for securing said support to a table, said securing means extending over a lower face of said support, said lower face being situated opposite said upper face.

8. The device according to claim 1, wherein said support includes a strip of flexible material.

9. The device according to claim 1, further comprising a plurality of surgical suturing threads associated with a plurality of needles, said suturing threads and needles being attached to said support, wherein said support comprises means to display at least one technical characteristic particular to each suturing thread or each needle to be stored.

10. The device according to claim 1, wherein the at least one technical characteristic of said suturing thread or said needle corresponds to at least one of a diameter, shape, size, length, type, absorbability, and cross-sectional shape of said suturing thread or said needle.

11. The device according to claim 1, wherein said attachment means extends over at least half of said upper face of said support.

12. The device according to claim 1, wherein said attachment means is selected from the group consisting of a longitudinally-extending adhesive surface, and a slot formed in said support.

13. The device according to claim 1, wherein said self-fastening strip is selected from the group consisting of a hook and loop fastener, and a material having channels to removably retain said suturing thread or said remnant.

14. The device according to claim 1, wherein said indicator is separate and removable from said support.

15. A system for storing, classifying, or arranging surgical suturing threads or surgical suturing threads mounted to needles, the system comprising:

a support having an upper face carrying a self-fastening strip adapted to removably attach with and temporarily secure at least one surgical suturing thread or at least one remnant of a suturing thread, such that said suturing thread or remnant is selectively removable from said self-fastening strip and usable in a surgical procedure, said support comprising attachment means for temporarily connecting with parts of multiple sterile packs;

wherein said parts of said multiple sterile packs are attached to said attachment means, each of said parts including an indicator with information conveying to the user at least one technical characteristic particular to said suturing thread or said needle to be stored, said technical characteristic corresponding to at least one of a diameter, shape, size, length, type, absorbability, and cross-sectional shape of said suturing thread or said needle, said sterile packs housing said suturing thread and/or said needle prior to attachment with said support.

16. The system of claim 15, further comprising means to receive a tip of said needle, said means extending over said upper face of said support, in the vicinity of said self-fastening strip.

* * * * *